United States Patent [19]

Hell et al.

[11] Patent Number: 5,548,630
[45] Date of Patent: Aug. 20, 1996

[54] X-RAY RADIATOR HAVING AN ELECTRON SOURCE FOR SENDING A BEAM OF ELECTRONS ALONG AN ELONGATED ANODE

[75] Inventors: Erich Hell, Erlangen; Manfred Fuchs, Nuremberg, both of Germany

[73] Assignee: Siemens Aktiengesellschaft, Munich, Germany

[21] Appl. No.: 521,365

[22] Filed: Aug. 31, 1995

[30]    Foreign Application Priority Data

Sep. 16, 1994 [DE]   Germany ................ 44 33 133.9

[51] Int. Cl.⁶ ............................................. H01J 35/30
[52] U.S. Cl. ................................. 378/137; 378/121
[58] Field of Search ................................. 378/119, 121, 378/137, 138, 143, 113

[56]    References Cited

U.S. PATENT DOCUMENTS

| | | | |
|---|---|---|---|
| 2,394,070 | 2/1946 | Kerst | 378/119 X |
| 5,164,972 | 11/1992 | Krumme | 378/137 X |
| 5,247,556 | 9/1993 | Eckert et al. | |

FOREIGN PATENT DOCUMENTS

| | | |
|---|---|---|
| 0455177A2 | 11/1991 | European Pat. Off. . |
| 4103588C1 | 5/1992 | Germany . |
| 2044985 | 10/1980 | United Kingdom . |

*Primary Examiner*—David P. Porta
*Attorney, Agent, or Firm*—Hill, Steadman & Simpson

[57]    ABSTRACT

According to the invention, at least one magnet element is provided for generating a guide magnetic field such that the electrons are guided at a spacing from the elongated anode. At least one kicker magnet is provided for generating a kicker magnetic field such that the electrons are steered onto the elongated anode in the region of the kicker magnetic field. The kicker magnet is implemented as a permanent magnet.

19 Claims, 2 Drawing Sheets

X-RAY RADIATOR HAVING AN ELECTRON SOURCE FOR SENDING A BEAM OF ELECTRONS ALONG AN ELONGATED ANODE

BACKGROUND OF THE INVENTION

The invention is directed to an X-ray radiator having an electron source for generating a beam of electrons that are focussed along an elongated anode and that is provided with at least one kicker magnet for generating a kicker magnetic field such that the electrons are deflected onto the elongated anode in the region of the kicker magnetic field.

DE 41 03 588 C1 corresponding to U.S. Pat. No. 5,247,556 discloses a computer tomograph having an X-radiator that is implemented with a ring anode that is scanned by an electron beam for generating a rotating, fan-shaped X-ray beam. The electron beam is generated by an electron gun that is followed by focussing coils for focussing the electrons. A magnetic deflection coil is provided, via which the electrons are deflectable onto the ring anode. A control means controls the deflection coil in such a way that the electron beam penetrates the X-ray source concentrically relative to the ring anode before the beginning of a scan event until it impinges a radiation receiver at the closed end. Subsequently, the deflection coils deflect it onto the ring anode and it scans the latter from its one end to its other end. The X-radiator is approximately circularly designed.

GB 2 044 985 A discloses an X-radiator that likewise comprises an electron gun for generating an electron beam that extends along a ring anode. The electrons are guided along the anode and deflected thereunto by electrostatic means. A fan-shaped ray beam for scanning an examination subject is generated by scanning the annular anode with the deflected electron beam.

Given the X-radiator of DE 41 03 588, it is considered disadvantageous that energy is utilized by the drive of the deflection coil for deflecting the electron beam onto the anode. Furthermore, the deflection coil is involved in terms of manufacture.

Given the X-radiator of GB 2 044 895 A, the high voltages that must be applied to the electrostatic means present insulation problems.

EP-0 455 177 A2 discloses an annular X-ray generator wherein the electrons can be kicked out of their orbit by stationary electromagnets provided at the circumference of a ring arrangement. The stationary electromagnets are switched on or off for deflecting the electron beam along an elongated anode.

SUMMARY OF THE INVENTION

An object of the invention is to implement an X-radiator of the type initially cited such that it can be cost-beneficially manufactured given little design expense; in particular, the electron beam should be deflectable on the anode in a simple way and without great expense.

This object is achieved according to the invention in that the kicker magnet is seated in mechanically adjustable fashion along the elongated anode.

In the X-radiator of the invention, the kicker magnet can be adjusted along the anode with low mechanical expense. The costs are reduced since only one kicker magnet is provided. It is especially advantageous when the kicker magnet is implemented as a permanent magnet. Compared to the Prior Art, no electromagnet coils to which energy must be supplied for the deflection of the electron beam are provided. Moreover, a permanent magnet is simple to manufacture and can be advantageously adjusted along the anode in a structurally simple way.

An advantage of this embodiment is that a structurally simply constructed deflection coil can be employed for the deflection of the electrons along the elongated anode.

Further advantages and details of the invention result from the following description of an X-radiator of the invention with reference to the drawings figures.

DESCRIPTION OF THE PREFERRED EMBODIMENTS

Figure 1:
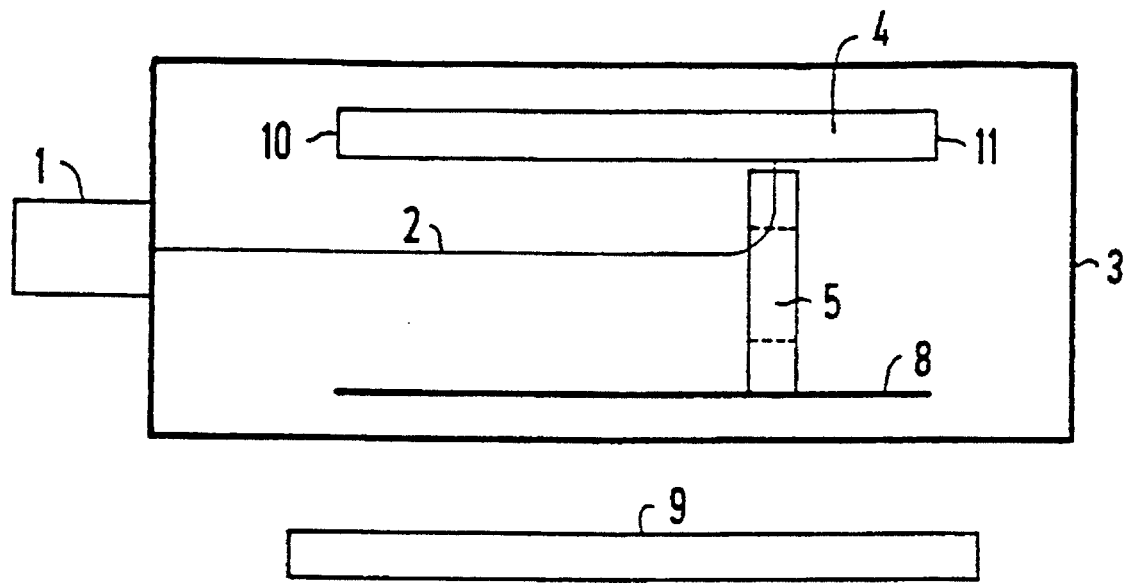
FIG. 1 is a first exemplary embodiment of an X-radiator of the invention in a side view.
Figure 2:
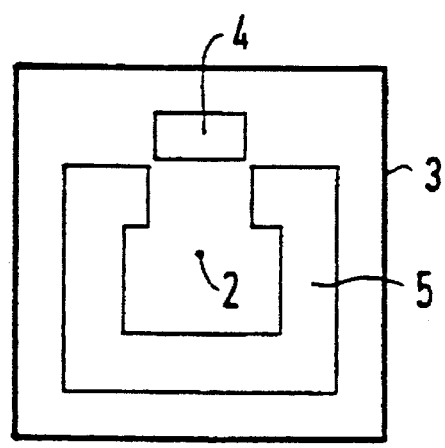
FIG. 2 is the exemplary embodiment of FIG. 1 in crossection.

FIGS. 1 and 2 schematically show an exemplary embodiment of an X-radiator of the invention that comprises an electron source 1 for coupling a beam of electrons 2 into a vacuum vessel 3. An elongated anode 4, which is rod-shaped in the exemplary embodiment, as well as a permanent magnet 5 according to the invention as a kicker magnet for generating a kicker magnetic field are arranged in the vacuum vessel 3. A magnet element 6 for generating a guide magnetic field 7 and/or a focussing means can be provided inside or outside the vacuum vessel 3 such that the electrons are guided at an interval from the elongated anode 4 as an electron beam. The magnet element 6 is required, given an annular anode arrangement, but is not compulsory given a linear anode arrangement.

The magnetic field of the permanent magnet 5 is aligned as a kicker magnetic field such that the electrons 2 are steered onto the elongated anode 4 for generating X-radiation.

Within the scope of the invention, the permanent magnet 5 or an electromagnet as well can be seated in adjustable fashion along a guide rail 8. For adjusting the permanent magnet 5 along the guide rail 8, a magnet unit 9 for generating a magnetic field is provided outside the vacuum vessel 3 such that the permanent magnet 5 is adjusted along the guide rail 8 by the magnetic field emanating from the magnet unit 9. For this purpose, the magnet unit 9 can comprise an adjustable permanent magnet or individually drivable electromagnet elements. The position of the permanent magnet 5 can thus be set along the elongated anode 4. It is thus possible to deflect the electrons 2 along the anode 4 from one end 10 to the other end 11 as well as in the opposite direction, so that a locationally variable ray beam can be generated. An arrangement of electromagnets for generating a travelling field with which the electrons 2 can be steered onto the rod-shaped anode 4 from the end 10 to the end 11 and in the opposite direction can also be provided for deflecting the electrons 2.

The energy for deflecting the electron beam can be advantageously supplied to an adjustable electromagnet inductively, or via wiper rings.

A combination of a permanent magnet for the adjustment or deflection with an electromagnet for the deflection or adjustment likewise lies within the scope of the invention.

Figure 3:
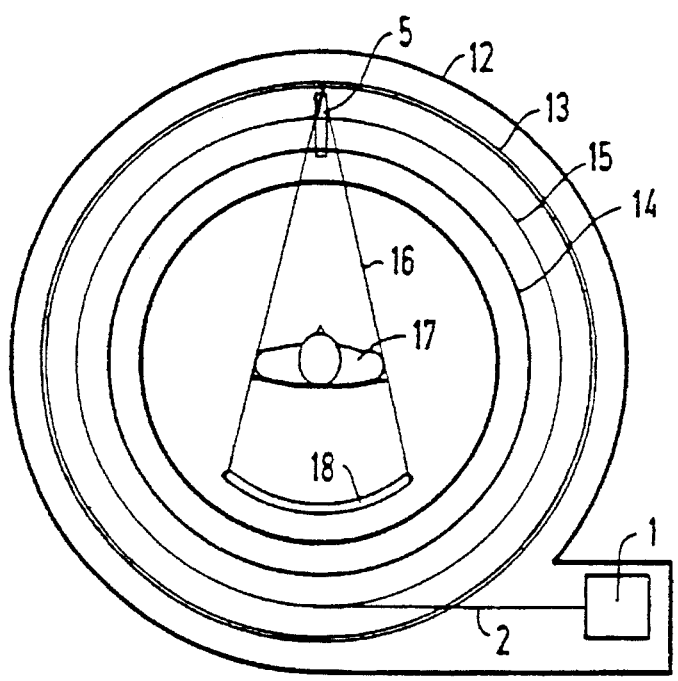
FIG. 3 is a second exemplary embodiment of an X-radiator of the invention.

FIG. 3 shows a further exemplary embodiment of an X-radiator of the invention, whereby a likewise annular anode 13 as well as a permanent magnet 5 according to the invention adjustably seated at an annular guide rail 14 are arranged in an annular vacuum vessel 12. An electron source is likewise referenced 1 and serves the purpose of generating electrons 2 and coupling them into the annular vacuum vessel 12. The electrons 2 are forced onto an annular electron orbit 15 by at least one magnet element, preferably by a plurality of magnet elements 6 arranged outside the annular vacuum vessel 12, this electron orbit 13 being spaced from the annular anode 13. A magnet means (not shown) for the adjustment of the permanent magnet 5 along the annular guide rail 14 is likewise provided outside the annular vacuum housing 12. Dependent on the position of the permanent magnet 5, the electrons 2 can, as shown, also be steered onto the annular anode 13 for generating a ray beam 16. Due to the adjustment of the permanent magnet 5 along the annular guide rail 14 as a result of a rotary or moving magnetic field emanating from the magnet means, a rotating ray beam 16 is also generated, for example for scanning an examination subject 17 arranged in the center of the X-radiator. In a way known in computer tomography, the ray beam impinges a detector line 18 arranged lying opposite the permanent magnet 5 and rotates around the center of the X-radiator together with the permanent magnet, or can be designed as a ring. As already initially set forth, the permanent magnet 5 can be replaced by an adjustable electromagnet or by a combination of permanent magnet and electromagnet within the scope of the invention.

Figure 4:
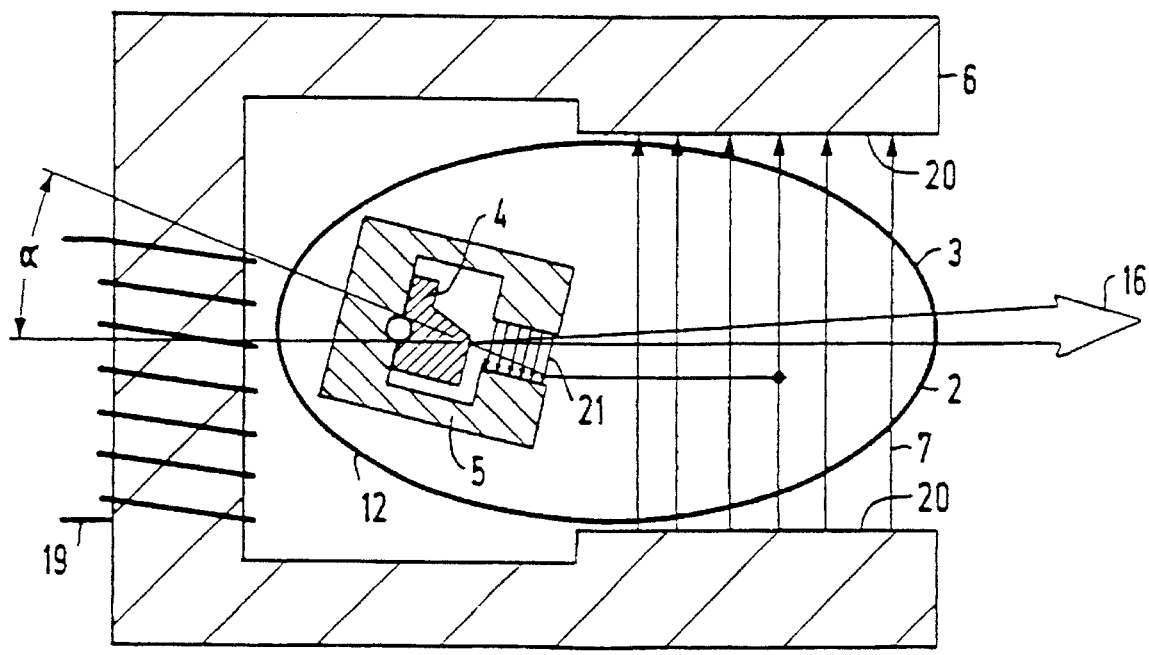
FIG. 4 is a crossection through the X-radiator of FIGS. 1–3 with a tilted kicker magnetic field.

Elements that have already been provided with reference characters in FIGS. 1–3 are provided with the same reference characters in FIG. 4. It follows from FIG. 4 that the magnet element 6 is implemented as an electromagnet and comprises a coil 19 that can be driven by a drive means (not shown). The magnet element 6 thus comprises a U-shaped core from whose pole ends 20 the guide magnetic field proceeds. In the region of the permanent magnet 5, the magnetic fields 21 emanating from the permanent magnet 5 act on the electrons 2 as a kicker magnetic field, so that these electrons 2 are steered out of their orbit onto the anode 13. The kicker magnetic field 21 can be tilted antiparallel or tilted with reference to the guide magnetic field 7 such that the electrons 2 impinge the surface of the anode 13 in optimally perpendicular fashion. The tilt should preferably be selected such that a circular focal spot is generated on the anode 13 from an elliptically shaped electron beam 2.

Within the scope of the invention, a plurality of magnet elements 6 following one another can generate a static or, on the other hand, a dynamic guide magnetic field 7. It is possible to provide only a single permanent magnet 5 adjustable along the anode 4, 13, or on the other hand, to arrange a plurality of permanent magnets 5 following one another along the anode 4,13 and to effect the deflection of the electrons 2 onto the anode 4,13 in that the correspondingly allocated magnet element 6 emits no guide magnetic field 7 at a predetermined location of the anode 4, so that the electrons 2 are steered onto the anode 4 at this location due to the influence of the kicker magnetic field 21. A rotating ray beam 16 can likewise be generated by successive drive of the magnet elements 6 of such an arrangement. What is thus critical to the invention is that a dynamic guide magnetic field 7 and a static kicker magnetic field 21 are utilized for the deflection of the electrons.

Within the scope of the invention, the magnet element 6 can be replaced by an electrode system.

Although various minor changes and modifications to the presently preferred embodiments described herein will be apparent to those skilled in the art, such changes and modifications can be made without departing from the spirit and scope of the present invention and without diminishing its intended advantages. Therefore, the appended claims are intended to cover such changes and modifications.

We claim as our invention:

1. An x-ray radiator, comprising:

an electron source for generating a beam of electrons that are focussed along a longitudinal extent of an elongated anode;

at least one kicker magnet for generating a kicker magnetic field such that the electrons are deflected onto the elongated anode in a region of the kicker magnetic field; and the kicker magnet being seated in mechanically adjustable fashion along the longitudinal extent of the elongated anode.

2. An x-ray radiator according to claim 1, wherein the kicker magnet comprises an electromagnet.

3. An x-ray radiator according to claim 1, wherein the kicker magnet comprises a permanent magnet.

4. An x-ray radiator according to claim 1, wherein the kicker magnet comprises a permanent magnet for the adjustment along the elongated anode and an electromagnet for the deflection of the electrons.

5. An x-ray radiator according to claim 1, wherein the kicker magnet comprises an electromagnet for the adjustment along the elongated anode and a permanent magnet for the deflection of the electrons.

6. An x-ray radiator according to claim 1 comprising at least one magnet element for generating a guide magnetic field such that the electrons are guided at a spacing from the elongated anode.

7. An x-ray radiator according to claim 6, wherein the magnet element is formed by a plurality of separate, discrete elements.

8. An x-ray radiator according to claim 7, wherein the discrete elements are electromagnets which are individually driven for generating a dynamic guide magnetic field.

9. An x-ray radiator according to claim 6, wherein the magnet element is formed by a permanent magnet.

10. An x-ray radiator according to claim 6, wherein the kicker magnetic field is tilted relative to the guide magnetic field.

11. An x-ray radiator according to claim 6, wherein the kicker magnetic field is tilted relative to the guide magnetic field such that the electrons generate an at least approximately circular focal spot on the anode.

12. An x-ray radiator according to claim 6, wherein the kicker magnetic field is aligned antiparallel to the guide magnetic field.

13. An x-ray radiator according to claim 1, wherein the elongated anode is rod-shaped.

14. An x-ray radiator according to claim 1, wherein the elongated anode is arcuate.

15. An x-ray radiator according to claim 1, wherein the elongated anode comprises a ring.

16. An x-ray radiator according to claim 1, wherein the radiator comprises a computer tomograph.

17. An x-ray radiator according to claim 1 further including a magnet unit spaced from said kicker magnet for exerting a magnetic field for mechanically adjustably moving the kicker magnet along the longitudinal extent of the elongated anode.

18. An x-ray radiator, comprising:

a vacuum vessel having an elongated anode therein for generating X-rays, a guide path spaced from and parallel to said elongated anode;

an electron source for generating and radiating an electron beam into said vacuum vessel;

a kicker magnet for generating a kicker magnetic field for deflecting said electron beam entering into said vacuum vessel in a direction parallel to said elongated anode such that the electron beam is bent toward the elongated anode at said kicker magnet, said kicker magnet being adjustably movable along said guide path and thus along the elongated anode; and a magnetic unit external to said vacuum vessel for creating a magnetic field for adjustably positioning said kicker magnet along said guide path.

19. An X-ray radiator according to claim 18, wherein said kicker magnet comprises a first magnet for deflecting said beam of electrons toward said elongated anode and a second magnet which is acted upon by said magnet unit for adjustable positioning of said kicker magnet along said guide path.

* * * * *